United States Patent
Bai et al.

(10) Patent No.: US 12,148,160 B2
(45) Date of Patent: Nov. 19, 2024

(54) METHOD FOR QUANTITATIVELY MEASURING THE WATER EXCHANGE RATE ACROSS MYELIN SHEATH IN BRAIN WHITE MATTER

(71) Applicant: ZHEJIANG UNIVERSITY, Hangzhou (CN)

(72) Inventors: Ruiliang Bai, Hangzhou (CN); Zhaoqing Li, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/579,858

(22) PCT Filed: Dec. 6, 2022

(86) PCT No.: PCT/CN2022/136740
§ 371 (c)(1),
(2) Date: Jan. 16, 2024

(87) PCT Pub. No.: WO2023/104000
PCT Pub. Date: Jun. 15, 2023

(65) Prior Publication Data
US 2024/0265538 A1    Aug. 8, 2024

(30) Foreign Application Priority Data
Dec. 7, 2021   (CN) .......................... 202111482739.7

(51) Int. Cl.
*G06T 7/00*     (2017.01)
*G06T 7/73*     (2017.01)
*G16H 30/40*    (2018.01)

(52) U.S. Cl.
CPC .............. *G06T 7/0012* (2013.01); *G06T 7/73* (2017.01); *G16H 30/40* (2018.01);
(Continued)

(58) Field of Classification Search
CPC ..................... G06T 7/0012; G06T 7/73; G06T 2207/10088; G06T 2207/30016;
(Continued)

(56) References Cited

U.S. PATENT DOCUMENTS

2005/0068031 A1* 3/2005 Frank ............... G01R 33/56341
                                                              324/309
2019/0365273 A1   12/2019 Jara

FOREIGN PATENT DOCUMENTS

CN   110391016   10/2019
CN   111751770   10/2020
(Continued)

OTHER PUBLICATIONS

Noninvasive Mapping of Water Diffusional Exchange in the Human Brain Using Filter-Exchange Imaging (Year: 2013).*

*Primary Examiner* — Vu Le
*Assistant Examiner* — Winta Gebreslassie
(74) *Attorney, Agent, or Firm* — Jiwen Chen; Joywin IP Law PLLC

(57) ABSTRACT

This invention discloses a method for quantitatively measuring the water exchange rate across myelin sheath. The method involves the following steps: acquiring images using the FEXI sequence; identifying anisotropic regions and the orientation of neural fibers at each pixel within these regions; selecting images where the diffusion weighted directions are perpendicular to the orientation of neural fibers at each pixel within the anisotropic regions and numerically averaging the selected images; calculating the apparent exchange rate (AXR), the apparent diffusion coefficient (ADC), and the filter coefficient (σ) using the numerically averaged images, where AXR serves as a specific parameter reflecting the water exchange rate across myelin sheath. The method provided by this invention enables specific detection of the exchange process of water mol- (Continued)

ecules inside and outside the myelin sheath and analysis of the apparent water exchange rate across myelin sheath.

8 Claims, 3 Drawing Sheets

(52) U.S. Cl.
CPC ............... *G06T 2207/10088* (2013.01); *G06T 2207/30016* (2013.01); *G06T 2207/30024* (2013.01)

(58) Field of Classification Search
CPC ........... G06T 2207/30024; G06T 2207/10092; G16H 30/40; A61B 6/504; A61B 5/7275; A61B 5/0042; A61B 2576/026; A61B 5/4088; A61B 5/6868
See application file for complete search history.

(56) References Cited

FOREIGN PATENT DOCUMENTS

| | | |
|---|---|---|
| CN | 113257430 | 8/2021 |
| CN | 113406546 | 9/2021 |

\* cited by examiner

METHOD FOR QUANTITATIVELY MEASURING THE WATER EXCHANGE RATE ACROSS MYELIN SHEATH IN BRAIN WHITE MATTER

This is a U.S. national stage application of PCT Application No. PCT/CN2022/136740 under 35 U.S.C. 371, filed Dec. 6, 2022 in Chinese, claiming priority of Chinese Application No. 202111482739.7, filed Dec. 7, 2021, all of which are hereby incorporated by reference.

TECHNICAL FIELD

The present invention relates to the field of magnetic resonance imaging, particularly to a method for quantitatively measuring the water exchange rate across myelin sheath in brain white matter.

BACKGROUND TECHNOLOGY

The water exchange rate across myelin sheath is a potential medical imaging indicator that can reflect the integrity of the myelin sheath and changes in axonal microstructure (Nedjati-Gilani et al. 2017; Hill et al. 2021). Developing a method for quantitatively measuring the water exchange rate across myelin sheath is crucial for understanding diseases that involve myelin sheath pathology, such as multiple sclerosis. Currently, clinically feasible techniques for measuring brain water transmembrane exchange rate in-vivo include (1) methods based on contrast agents in magnetic resonance imaging (MRI), such as Dynamic Contrast-Enhanced MRI (DCE-MRI). (2) Filter-exchange imaging (FEXI) based on diffusion MRI. The first method is primarily used for measuring the water exchange rate across blood-brain barrier, as in the Chinese patent application CN110391016A. The second method, FEXI, has demonstrated the ability to measure the water exchange rate across blood-brain barrier due to the flexibility of its imaging sequence, as in the Chinese patent application CN111751770A. However, there is still a lack of a feasible method that can specifically measure the water exchange rate across myelin sheath.

SUMMARY OF THE INVENTION

The object of the present invention is to provide a method for quantitatively measuring the exchange rate of water molecules inside and outside the myelin sheath of the brain. The method provided by the present invention can realize specific detection of the exchange process of water molecules inside and outside the myelin sheath, and analyze the apparent exchange rate constant of water molecules inside and outside the myelin sheath.

To achieve the above-mentioned purpose, the present invention adopts the following technical solution:

A method for quantitatively measuring the water exchange rate across myelin sheath in brain white matter, including:
(1) acquiring brain images in multi-diffusion weighted directions by exchanging the filtered magnetic resonance imaging FEXI sequence;
(2) according to a part of the images acquired in the step (1), determining the brain white matter area with anisotropic structure in the image, referred to as the anisotropic area, and determining the direction of the nerve fibers of each pixel in the anisotropic area;
(3) from all the images acquired in the step (1), selecting images that are perpendicular to the direction of the nerve fibers of each pixel in the anisotropic area;
(4) calculating the apparent water exchange rate (AXR), apparent diffusion coefficient (ADC) and filtering coefficient (σ) of each pixel in the anisotropic area on the image by using the image selected in the step (3), where AXR serves as a parameter reflecting the exchange rate of water molecules inside and outside the myelin sheath.

The method provided by the present invention includes two main parts: data acquisition in step (1) and data analysis in steps (2-4).

In step (1), the magnetic resonance imaging FEXI sequence includes a filter module, an exchange module, and a detection module. Both the filter and detection modules employ a single Pulsed Gradient Spin Echo (PGSE) sequence. The filter module sets appropriate diffusion-weighted b value and multiple diffusion weighted directions. The exchange module sets the exchanging time ($t_m$). The detection module sets suitable diffusion-weighted b value and multiple diffusion weighted directions for detecting the MRI signals after the exchanging time $t_m$. In each image acquisition, the diffusion-weighted b value in the filter and detection modules are kept the same direction.

In step (1), the magnetic resonance imaging FEXI sequence acquires images under different diffusion weighted directions and two image acquisitions in each diffusion weighted direction. In the first image acquisition, the filter module uses non-zero diffusion-weighting b value ($b_f > 0$), the exchanging time of the exchange module is set as $t_m$ for measurement, and the detection module employs two b values, b1 and b2, to acquire MRI signals, denoted as $S(t_m, b_1)$ and $S(t_m, b_2)$. In the second image acquisition, the filter module uses zero diffusion-weighting b value ($b_f = 0$ s/mm$^2$), the exchanging time of the exchange module is set as the shortest value, and the diffusion weighting of the detection module includes two b values, which are b1 and b2. The settings are the same as the first image acquisition. The magnetic resonance signals $S_0(b_1)$ and $S_0(b_2)$ are obtained, respectively.

Preferably, setting the shortest echo time (TE) in the filter and detection modules can enhance image signal-to-noise ratio.

Preferably, in the first image acquisition, the filter module employs a non-zero diffusion-weighting $b_f$ value ranging from 800 s/mm$^2$ to 1300 s/mm$^2$.

Preferably, the values of exchanging time ($t_m$) in the exchange module range from the shortest value to 1000 ms.

Preferably, the exchange module sets multiple ($>=2$) exchanging time for measurements.

Preferably, in the detection module, $b_1$ is set as a value ranging from 100 s/mm$^2$ to 250 s/mm$^2$, and $b_2$ is set as a value ranging from 800 s/mm$^2$ to 1300 s/mm$^2$.

Preferably, the diffusion weighted directions for the filter and detection modules should be set to equal or greater than six directions.

In step (2), for each pixel within anisotropic regions, the diffusion tensor is obtained by using the FEXI sequence to perform nonlinear least squares fitting on the data $b_f = 0$ s/mm$^2$ acquired in multiple diffusion weighted directions. The principal eigenvector of the diffusion tensor corresponds to the orientation of neural fibers at that pixel. Specifically:

The FEXI sequence uses a zero diffusion-weighting b value ($b_f = 0$ s/mm$^2$) in the filter module, the shortest exchanging time in the exchange module, and the diffusion weighting of the detection module includes two b-value images, and the diffusion tensor of each pixel is fitted by the nonlinear least squares method. The pixels with fractional anisotropy (FA) values between 0.35 and 1 and mean diffusivity (MD) values between 0.5 and 1.3 μm²/ms are determined as anisotropic regions. The principal eigenvector of the diffusion tensor is calculated for each pixel in anisotropic regions and represents the orientation of neural fibers.

Method 1: In the step (3), for each pixel within the white matter region (anisotropic region) of the image, selecting datasets from the images where the angle between the diffusion weighted direction and the neural fiber (bundles of axons) orientation at that pixel are in the range of 75° to 105°. If the number of the selected diffusion weighted direction perpendicular to the nerve fiber orientation of the pixel point (the included angle is between 75° and 105°) is equal to 0, the measurement of water exchange rate across myelin sheath for that pixel is omitted. If the number of the selected diffusion weighted direction perpendicular to the nerve fiber orientation of the pixel point (the included angle is between 75° and 105°) is equal to 1, the selected datasets are used for the subsequent fitting steps to obtain AXR, ADC, and σ, where AXR represents a constant reflecting the exchange rate of water molecules inside and outside the myelin sheath. If the number of the selected diffusion weighted direction perpendicular to the nerve fiber orientation of the pixel point (the included angle is between 75° and 105°) is greater than 1, all the selected datasets from different diffusion weighted directions are averaged. This involves averaging the datasets acquired under different diffusion weighted directions with various diffusion weighting factors ($b_f$), different exchanging times ($t_m$), and different diffusion-weighting blocks (b), respectively.

Method 2: In the step (3), from all datasets collected in step 1, selecting images where images perpendicular to the direction of the nerve fibers of each pixel in the anisotropic region, including:

(3-1) respectively calculating the angles between each diffusion weighted direction applied in the step (1) and the neural fiber orientation of each pixel within the anisotropic regions. Retaining the FEXI images where the angle between the diffusion weighted direction and the neural fiber orientation is ≥165° and ≤180° or angles ≥0° and ≤15°.

(3-2) If the number of selected dataset where the diffusion weighted direction perpendicular to neural fiber orientation in the pixel is zero, skipping the measurement of water exchange rate across myelin sheath for that pixel. If the number equals 1, then the FEXI images corresponding to the diffusion weighted direction are used in step (4). If the number is greater than 1, then the FEXI images corresponding to these diffusion weighted directions are numerically averaged and used in step (4), wherein FEXI images under different $b_f$, different $t_m$ and different $b_d$ are averaged, respectively.

In step (4), the apparent diffusion coefficient ADC'($t_m$) for different $t_m$ values is calculated, and then the least square method is used for the formula ADC'($t_m$)=ADC(1−σexp(−$t_m$AXR)) to obtain AXR, ADC, and σ, wherein AXR represents a constant reflecting the exchange rate of water molecules inside and outside the myelin sheath.

ADC' ($t_m$) is calculated by using the formula $$ADC'(t_m) = -\frac{1}{b_2 - b_1} \ln\left(\frac{\frac{1}{M}\sum_{i=0}^{M} S_i(t_m, b_2)}{\frac{1}{M}\sum_{i=0}^{M} S_i(t_m, b_1)}\right),$$

where $S_i(t_m, b_1)$ and $S_i(t_m, b_2)$ are data whose diffusion weighted direction of the i-th group is perpendicular to the direction of nerve fibers, which correspond to the two diffusion weighted magnetic resonance signals obtained by image acquisition;

wherein, the apparent diffusion coefficient at equilibrium, ADC'($t_m=\infty$), is obtained by using the formula $$ADC'(t_m = \infty) = -\frac{1}{b_2 - b_1} \ln\left(\frac{S_0(b_2)}{S_0(b_1)}\right),$$

where the exchanging time $t_m$ is considered infinite, i.e., $t_m=\infty$. M represents the number of diffusion weighted directions perpendicular to the neural fiber orientation of the pixel point (M≥1).

When the FEXI image in which the diffusion weighted direction is perpendicular to the neural fiber orientation in method 1 is used, the constant reflecting the exchange rate of axonal water molecules is calculated;

When the FEXI image in which the diffusion-weighted direction is perpendicular to the neural fiber orientation in the second method is used, the calculation reflects the exchange rate of water molecules in the glial cells and intercellular water molecules in the white matter.

Preferably, in step (2), a multi-directional diffusion-weighted Diffusion Tensor imaging (DTI) image can be used to acquire images, separately, to determine anisotropic regions and calculate the neural fiber orientations of each pixel within the anisotropic regions.

Preferably, in step (2) and step (3), image pre-processing can be applied, including eddy current correction, motion correction, etc.

The method provided by the present invention allows for specific detection of the exchange process of water molecules within and outside the myelin sheath and enables the analysis of the water exchange rate across myelin sheath.

SPECIFIC EMBODIMENTS OF THE INVENTION

In order to make the purpose, technical solutions, and advantages of the present invention clearer, the technical solutions of the present invention will be described clearly and comprehensively below accompanied with figures:

The method provided by the present invention does not require the use of magnetic resonance contrast agents. The present invention employs the Filter-exchange imaging (FEXI) sequence based on diffusion MRI. By using multiple diffusion weighted directions in the filter and detection modules, the present invention achieves specific detection of water exchange processes across the myelin sheath.

Figure 2:
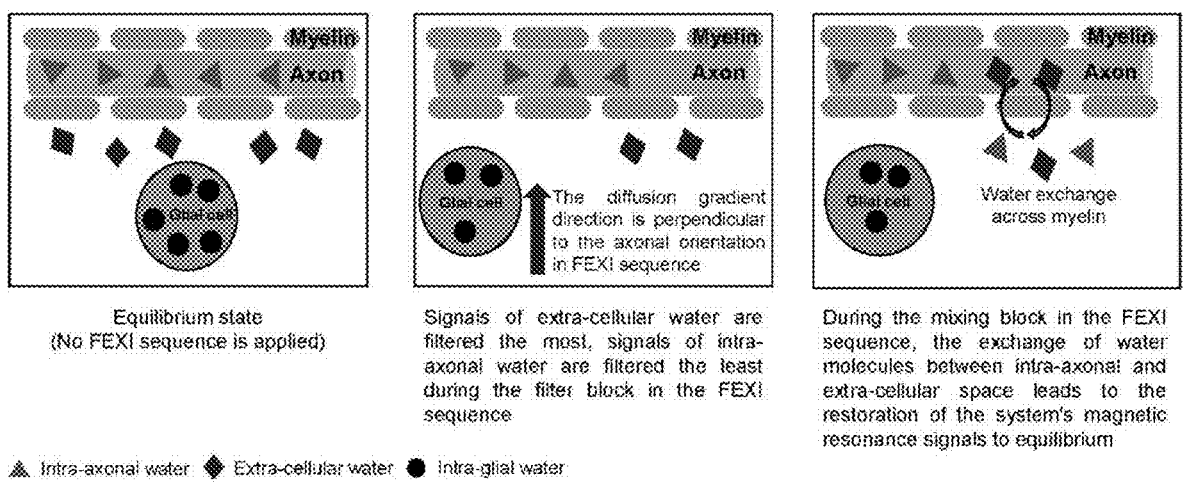
FIG. 2 illustrates the principle of measuring the water exchange rate across myelin sheath using the FEXI sequence with a specific diffusion gradient direction.
Figure 3:
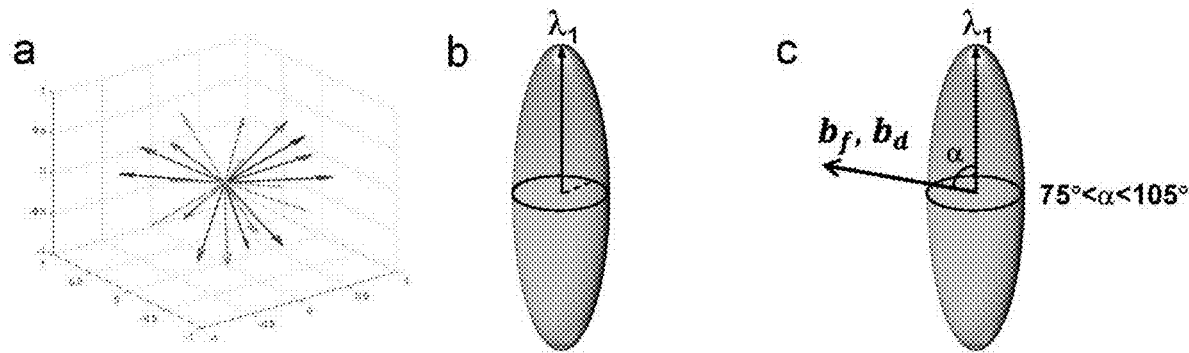
FIG. 3 depicts a schematic diagram of the method for measuring the water exchange rate across myelin sheath using the FEXI sequence with a specific diffusion gradient direction.

The technical principle of the present invention is based on the fact that the brain white matter mainly consists of axons enveloped by myelin sheath and glial cells. Water molecules within the white matter can be roughly categorized into three components based on their locations: namely, water molecules in axons, water molecules in glial cells, and water molecules outside axons and glial cells (hereinafter referred to as cells), interstitial water molecules). Due to differences in the microstructure of their locations, they exhibit variations in apparent diffusion coefficient (ADC). Specifically, axons have oriented shapes in space, whereas glial cells generally lack a specific orientation in spatial morphology. The anisotropy of axonal structures results in different ADC when different diffusion weighted directions are applied. When diffusion weighted gradient direction is parallel to the orientation of axon (neural fiber), the detected ADC is higher than when diffusion weighted gradient direction is perpendicular to the orientation of axon (neural fiber). Glial cells, due to their spatially non-specific structure, exhibit no significant difference in ADC under different diffusion weighted directions. By utilizing these differences in ADC for water molecules in different structures under various diffusion weighted directions, the FEXI sequence generates direction-dependent AXR parameters. Specifically, when the diffusion weighted direction is perpendicular to the orientation of neural fiber, the diffusion weighting applied in the filtering module makes the detected apparent diffusion rate constants of water molecules in different structures different. Among them, the magnetic resonance signal filtering of water molecules in the intercellular space is the most, while the magnetic resonance signal filtering of water molecules in the myelin sheath is the least. According to the principle of FEXI, the AXR reflects the exchange between water molecules between two components with different diffusion-weighted sensitivities to the filtration module. The AXR obtained when the diffusion-weighted direction is perpendicular to the neural fiber orientation reflects the exchange of water molecules in the myelin sheath and in the intercellular space. This principle is illustrated in FIG. 2. In order to achieve the purpose of measuring the exchange rate of water molecules inside and outside the myelin sheath, the present invention designs the diffusion weighting in multiple directions in the filter module and exchange modules of the FEXI sequence, and determines the neural density of each pixel in the space through the diffusion weighting in multiple directions, and subsequently select dataset where the diffusion weighted direction is perpendicular to the neural fiber orientation (as illustrated in FIG. 3). Using the signals under different exchanging times, the apparent diffusion coefficient ADC' ($t_m$) is calculated for different exchanging times. A least square fitting method is applied to the ADC'($t_m$) values at different exchanging times, yielding the apparent exchange rate AXR, representing the apparent exchange rate of water molecules within and outside the myelin sheath.

Figure 1:
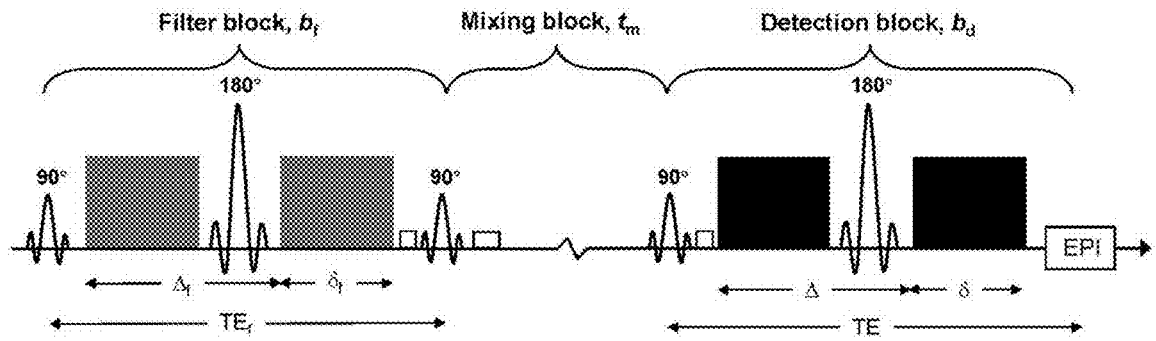
FIG. 1 shows a schematic diagram of the FEXI sequence.

FEXI can be used to measure the exchange rate of water molecules between two components with different diffusion coefficients. The FEXI sequence used in the present invention is shown in FIG. 1, which includes three blocks or modules: the filter block/module, the exchange block/module, and the detection block/module. Both the filter module and the detection module use a single Pulse Gradient Spin Echo (PGSE), with 20 diffusion weighted directions, as shown in FIG. 3(a). The diffusion weighted directions in the filter module and the detection module remain consistent in a single acquisition.

Figure 4:
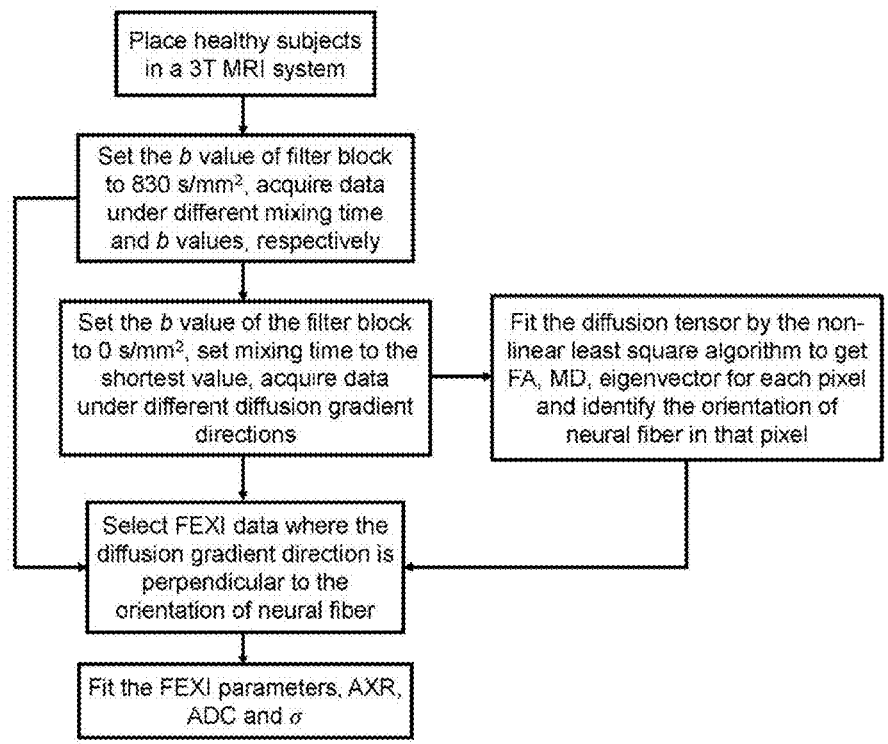
FIG. 4 presents a flowchart for an exemplary implementation.

As a specific example, the method provided by the present invention for measuring water exchange rate across myelin sheath is applied to the brain in healthy adults. The flowchart is shown in FIG. 4, and includes the following steps:

Step 1: Placing healthy subjects in a 3T MRI system with the center of the head as the scanning center and acquiring head images. In this exemplary embodiment, MRI data from eight healthy subjects were collected.

Step 2: Setting up the FEXI sequence with a resolution of 4×4 mm$^2$, a slice thickness of 4 mm, and positioning the corpus callosum at the center of the scanning Field of View (FOV) in the head-to-foot direction. A total of 12 slices were acquired. The diffusion weighting b value in the filter module was set to 830 s/mm$^2$, with the diffusion weighted direction set to one of the 20 directions shown in FIG. 3(a). The diffusion weighting b values in the detection module was set to 100 s/mm$^2$ ($b_1$) and 1300 s/mm$^2$ ($b_2$), with the direction set to one of the 20 directions shown in FIG. 3(a). The diffusion weighted directions in both the filter module and the detection module should be consistent in a single acquisition. Three different exchanging times ($t_m$) are set in the exchange module: 25 ms, 200 ms, and 400 ms for multiple measurements. The echo time ($TE_f$) in the filter module is set to 26 ms, and the echo time (TE) in the detection module is set to 37 ms. The time between the third 90° pulse in FIG. 1 and the start of the next sequence repeat is 2500 ms. This process is repeated by changing the diffusion weighted directions in the filter and exchange modules to acquire FEXI images for all 20 diffusion weighted directions.

Step 3: Changing the diffusion-weighted b value in the filter module to 0 s/mm$^2$ and set the exchanging time in the exchange module to the minimum (25 ms), keeping all other parameters the same. This process is repeated by changing the diffusion weighted directions in the filter and exchange modules to acquire FEXI images for all 20 diffusion weighted directions.

Step 4: Utilizing TORTOISE software to fit the diffusion tensor for the FEXI data obtained in the Step 3 by using a non-linear least square algorithm method. This will yield fractional anisotropy (FA), mean diffusivity (MD), and the principal eigenvector of the diffusion tensor at each pixel in the image. The first eigenvector of the diffusion tensor is considered to represent the orientation of neural fiber at the pixel.

Step 5: Identifying pixels with FA values in the range of 0.35 to 0.99 and MD values between 0.01 μm$^2$/ms and 1.0 μm$^2$/ms as the white matter regions (i.e., the aforementioned anisotropic regions). Based on the criteria illustrated in FIG. 3(c), at each white matter pixel, selecting FEXI datasets where the diffusion weighted directions are perpendicular to the orientation of neural fiber from the 20 diffusion weighted directions. If the number of selected FEXI datasets is zero, the AXR measurement for that pixel is omitted. If the number of selected FEXI datasets is one, the FEXI dataset from that direction is used for the fitting calculation in the Step 6. If the number of selected FEXI datasets is greater than one, the FEXI datasets corresponding to those directions are averaged for further fitting.

Step 6: Using the data obtained in the Step 5 to calculate the apparent diffusion coefficient (ADC'($t_m$)) for different $t_m$ values by using the formula $$ADC'(t_m) = -\frac{1}{b_2 - b_1} \ln\left(\frac{\frac{1}{M}\sum_{i=0}^{M} S_i(t_m, b_2)}{\frac{1}{M}\sum_{i=0}^{M} S_i(t_m, b_1)}\right),$$

where $S_i(t_m, b_1)$ and $S_i(t_m, b_2)$ represent data from ith diffusion weighted direction perpendicular to the orientation of neural fiber, and they correspond to magnetic resonance signals acquired in the detection module. Subsequently, using a non-linear least square method to fit the formula $ADC'(t_m) = ADC(1-\sigma\exp(-t_m AXR))$ to obtain apparent exchange rate (AXR), apparent diffusion coefficient (ADC), and filter coefficient ($\sigma$) for each pixel within the anisotropic regions. The AXR, obtained from FEXI data where the diffusion weighted direction perpendicular to the orientation of neural fiber, represents the water exchange rate across the myelin sheath.

Figure 5:
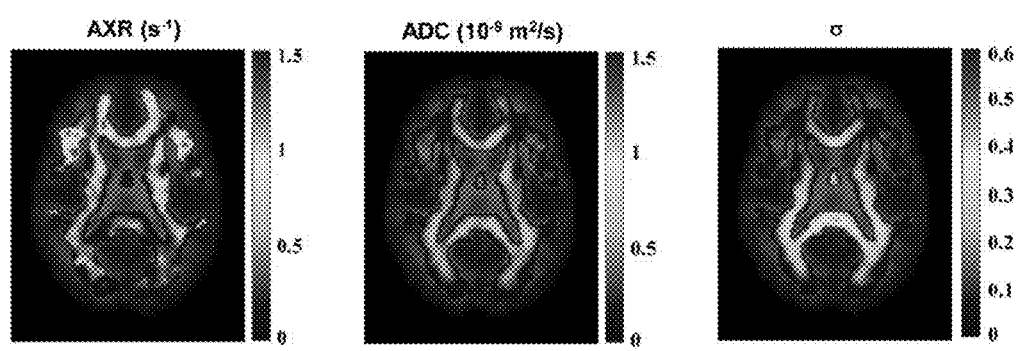
FIG. 5 displays the fitted apparent exchange rate (AXR), apparent diffusion coefficient (ADC), and filter coefficient (σ) in an exemplary implementation.

To demonstrate the effectiveness of the present invention in measuring the water exchange rate across myelin sheath, the experimental results for this specific embodiment will be illustrated in the accompanying figures. Taking the results of a single slice image on a cross-section of the brain as an example, FIG. 5 displays the apparent exchange rate (AXR), apparent diffusion coefficient (ADC), and filter coefficient ($\sigma$) fitted in the Step 6. The leftmost AXR image in FIG. 5 represents the parameter map reflecting the water exchange rate across myelin sheath. The underlay image is the fractional anisotropy (FA) image of a single slice, and the overlay image is the AXR map of anisotropic regions. From the image, it is qualitatively observed that there are differences in AXR values in different anisotropic regions, which may be related to the thickness of the myelin sheath in different regions. The relevant work of the present invention suggests that in neural fiber with thicker axonal myelin sheath sheaths, the AXR perpendicular to the neural fiber orientation is smaller, which proves that the AXR perpendicular to the white matter orientation reflects the exchange rate of water molecules inside and outside the myelin sheath. In addition, the relevant simulation experiment results of the present invention also show that the AXR perpendicular to the white matter can better reflect the exchange rate of water molecules inside and outside the myelin sheath.

The above-mentioned specific embodiments have described the technical solutions and beneficial effects of the present invention in detail. It should be understood that the above-mentioned are only the most preferred embodiments of the present invention, and are not intended to limit the present invention. Any modifications, supplements and equivalent substitutions made within the scope of the present invention should be included in the scope of protection of the present invention.

The invention claimed is:

1. A method for quantitatively measuring the water exchange rate across myelin sheath in brain white matter, characterized by the following steps:
   (1) acquiring brain images in multiple diffusion weighted directions by using Filter-exchange imaging (FEXI) sequence;
   (2) determining white matter region with anisotropic structure in the images according to a part of the images acquired in the step (1), referred to as an anisotropic region, and determining the direction of the neural fibers of each pixel in this region;
   (3) from all the images acquired in the step (1), selecting images perpendicular to orientation of neural fibers of each pixel in the anisotropic regions;
   (4) calculating an apparent exchange rate (AXR), an apparent diffusion coefficient (ADC), and a filter coefficient ($\sigma$) for each pixel within the anisotropic regions by using the images selected in the step (3), wherein the AXR reflects the water molecular exchange rate across myelin sheath;
   wherein, in the step (3), from all the images collected in step (1), selecting images where diffusion weighted directions are perpendicular to the orientation of neural fibers at each pixel within the anisotropic regions, comprising:
   (3-1) calculating the angles between each diffusion weighted direction applied in step (1) and the orientation of neural fibers at each pixel within the anisotropic regions; retaining the FEXI images where the angle between the diffusion weighted direction and the orientation of neural fibers is $\geq 75°$ and $\leq 105°$;
   (3-2) when the number of selected diffusion weighted directions perpendicular to the orientation of neural fibers at each pixel being 0, skipping the measurement of the water exchange rate across myelin sheath for that pixel; when the number being 1, using the FEXI image corresponding to that diffusion weighted direction for step (4); when the number is greater than 1, numerically averaging the FEXI images corresponding to these diffusion weighted directions for the step (4); wherein different FEXI images under different $b_f$, $t_m$, and $b_d$ settings are separately averaged;
   wherein, in the step (4), AXR, ADC, and $\sigma$ are obtained by using known $t_m$ and calculated apparent diffusion coefficient ADC'($t_m$) under different $t_m$, fitting the formula $ADC'(t_m) = ADC(1-\sigma\exp(-t_m AXR))$ using the non-linear least square method;
   ADC' ($t_m$) is calculated by using the formula $$ADC'(t_m) = -\frac{1}{b_2 - b_1} \ln\left(\frac{\frac{1}{M}\sum_{i=0}^{M} S_i(t_m, b_2)}{\frac{1}{M}\sum_{i=0}^{M} S_i(t_m, b_1)}\right),$$

where $S_i(t_m, b_1)$ and $S_i(t_m, b_2)$ are the magnetic resonance signals obtained under the filter module's non-zero diffusion-weighted $b_f$, exchange module's exchanging time $t_m$, and the ith set of diffusion weighted directions perpendicular to the orientation of neural fibers, corresponding to detection module's diffusion-weighted $b_1$ and $b_2$ settings; M represents the number of diffusion weighted directions perpendicular to the neural fiber orientation of the pixel point;
the steady-state apparent diffusion coefficient, ADC' ($t_m = \infty$) is obtained by using the formula $$ADC'(t_m = \infty) = -\frac{1}{b_2 - b_1} \ln\left(\frac{S_0(b_2)}{S_0(b_1)}\right),$$

wherein $S_0(b_1)$ and $S_0(b_2)$ are the magnetic resonance signals obtained under the filtering block's zero diffusion-weighted settings ($b_f=0$ s/mm$^2$), exchanging block's shortest exchanging time, and detection module's two diffusion-weighted settings $b_1$ and $b_2$, respectively;
wherein the AXR represents a constant reflecting the water exchange rate across myelin sheath in brain white matter;

when using the FEXI image whose diffusion weighted direction is perpendicular to the neural fiber orientation, the constant reflecting the axonal water molecule exchange rate is calculated.

2. The method for quantitatively measuring the water exchange rate across myelin sheath in brain white matter as described in claim 1, characterized by the following features: in the step (1), the FEXI sequence comprises a filter module, an exchange module, and a detection module; both the filter module and detection module use a single Pulsed Gradient Spin Echo (PGSE) sequence; appropriate diffusion-weighted b value is set in the filter module, and multiple diffusion weighted directions are used; the exchanging time ($t_m$) is set in the exchange module; the magnetic resonance signal is detected in the detection module after the exchange module, and the diffusion weighted directions of both filter module and detection module are kept consistent during each detection of the magnetic resonance signal.

3. The method for quantitatively measuring the water exchange rate across myelin sheath in brain white matter as described in claim 2, characterized by the following features: during images acquisition, images are collected along multiple diffusion weighted directions, and for each diffusion weighted direction, two sets of images are acquired using the FEXI sequence; in the first set of images, the filter module is set to a non-zero diffusion-weighted b value ($b_f$), the exchanging time in the exchange module is set to ($t_m$), and the detection module uses two different b values, referred to as $b_1$ and $b_2$, to obtain the magnetic resonance signals $S(t_m, b_1)$ and $S(t_m, b_2)$; in the second set of images, the filter module is set to a zero diffusion-weighted b value, the exchanging time in the exchange module is set to the shortest value, and the detection module uses the same b values as in the first set, $b_1$ and $b_2$, to obtain the magnetic resonance signals $S_0(b_1)$ and $S_0(b_2)$.

4. The method for quantitatively measuring the water exchange rate across myelin sheath in brain white matter as described in claim 3, characterized by the following features: in the first set of images collected in each diffusion weighted direction, the b value of the filter module is in the range from 800 s/mm² to 1300 s/mm²; the exchanging time ($t_m$) in the exchange module ranges from the shortest value to 1000 ms, and multiple exchanging time are set in the exchange module for multiple measurements.

5. The method for quantitatively measuring the water exchange rate across myelin sheath in brain white matter as described in claim 3, characterized by the following features: in the detection module, $b_1$ ranges from 100 s/mm² to 250 s/mm², and $b_2$ ranges from 800 s/mm² to 1300 s/mm².

6. The method for quantitatively measuring the water exchange rate across myelin sheath in brain white matter as described in claim 1, is characterized by the following features: in the step (2) of claim 1, determining anisotropic regions in the images and the orientation of neural fibers at each pixel within these anisotropic regions comprising:

(2-1) determining anisotropic regions in the images: using the FEXI sequence with the b value in the filter module set to 0, the exchanging time of the exchange module set to the shortest value, and the b value in the detection module set to two different values to acquire images which are used to fit the diffusion tensor at each pixel using non-linear least square algorithm to calculate the fractional anisotropy (FA) and mean diffusivity (MD) to determine anisotropic regions;

(2-2) determining the orientation of neural fibers at each pixel within anisotropic regions: calculating the first eigenvector of the diffusion tensor at each pixel within anisotropic regions as the orientation of neural fibers.

7. The method for quantitatively measuring the water exchange rate across myelin sheath in brain white matter as described in claim 6, characterized by the following features: in the step (2-1), pixels with FA values between 0.35 and 1 and MD values between 0.5 and 1.3 μm²/ms are determined as anisotropic regions.

8. A method for quantitatively measuring the water exchange rate across glial cells in brain white matter, characterized by the following steps:

(1) acquiring brain images in multiple diffusion weighted directions by using Filter-exchange Imaging (FEXI) sequence;

(2) determining white matter region with anisotropic structure in the images according to a part of the images acquired in the step (1), referred to as an anisotropic region, and determining the direction of the neural fibers of each pixel in this region;

(3) from all the images acquired in the step (1), selecting images parallel to orientation of neural fibers of each pixel in the anisotropic regions;

(4) calculating an apparent exchange rate (AXR), an apparent diffusion coefficient (ADC), and a filter coefficient (σ) for each pixel within the anisotropic regions by using the images selected in the step (3), wherein the AXR reflects the water molecular exchange rate across myelin sheath;

wherein, in the step (3), from all the images collected in the step (1), selecting images where diffusion weighted directions are parallel to the orientation of neural fibers at each pixel within the anisotropic regions, comprising:

(3-1) calculating the angles between each diffusion weighted direction applied in the step (1) and the orientation of the neural fibers at each pixel within the anisotropic regions; retaining the FEXI images where the angle between the diffusion weighted direction and the orientation of neural fibers is ≥165° and ≤180° or angles ≥0° and ≤15°;

(3-2) when the number of selected diffusion weighted directions parallel to the orientation of neural fibers at each pixel being 0, skipping the measurement of the water exchange rate across glial cells for that pixel; when the number being 1, using the FEXI image corresponding to that diffusion weighted direction for the step (4); when the number being greater than 1, numerically averaging the FEXI images corresponding to these diffusion weighted directions for step (4); wherein different FEXI images under different $b_f$, $t_m$, and $b_d$ settings are separately averaged;

wherein, in the step (4), AXR, ADC, and σ are obtained by using known $t_m$ and calculated apparent diffusion coefficient ADC'($t_m$) under different $t_m$, fitting the formula ADC'($t_m$)=ADC(1−σexp(−$t_m$AXR)) using the non-linear least square method;

ADC' ($t_m$) is calculated by using the formula $$ADC'(t_m) = -\frac{1}{b_2 - b_1} \ln\left(\frac{\frac{1}{M}\sum_{i=0}^{M} S_i(t_m, b_2)}{\frac{1}{M}\sum_{i=0}^{M} S_i(t_m, b_1)}\right),$$

where $S_i(t_m,b_1)$ and $S_i(t_m,b_2)$ are the magnetic resonance signals obtained under the filter module's non-zero diffusion-weighted $b_f$, exchange module's exchanging time $t_m$, and the ith set of diffusion weighted directions perpendicular to the orientation of neural fibers, corresponding to detection module's diffusion-weighted $b_1$ and $b_2$ settings; M represents the number of diffusion weighted directions parallel to the neural fiber orientation of the pixel point;

the steady-state apparent diffusion coefficient, ADC' ($t_m=\infty$) is obtained by using the formula $$ADC'(t_m = \infty) = -\frac{1}{b_2 - b_1}\ln\left(\frac{S_0(b_2)}{S_0(b_1)}\right),$$

wherein $S_0(b_1)$ and $S_0(b_2)$ are the magnetic resonance signals obtained under the filtering block's zero diffusion-weighted settings ($b_f=0$ s/mm$^2$), exchanging block's shortest exchanging time, and detection module's two diffusion-weighted settings $b_1$ and $b_2$, respectively;

wherein the AXR represents a constant reflecting the water exchange rate across myelin sheath in brain white matter;

when using the FEXI image in which the diffusion weighted direction is parallel to the orientation of the neural fibers, the calculation reflects the exchange rate of water molecules in the glial cells and intercellular water molecules in the white matter.

* * * * *